(12) United States Patent
Yeh et al.

(10) Patent No.: US 8,450,232 B2
(45) Date of Patent: May 28, 2013

(54) CATALYSTS USEFUL FOR THE ALKYLATION OF AROMATIC HYDROCARBONS

(75) Inventors: Chuen Yuan Yeh, Edison, NJ (US);
Ruozhi Song, Wilmington, DE (US);
Anne Mae Gaffney, West Chester, PA (US); Tadeusz Langner, Maplewood, NJ (US); Marshall J. Margolis, Freehold, NJ (US)

(73) Assignee: Lummus Technology Inc., Bloomfield, NJ (US)

( * ) Notice: Subject to any disclaimer, the term of this patent is extended or adjusted under 35 U.S.C. 154(b) by 952 days.

(21) Appl. No.: 12/353,693

(22) Filed: Jan. 14, 2009

(65) Prior Publication Data
US 2010/0179359 A1 Jul. 15, 2010

(51) Int. Cl.
*B01J 29/06* (2006.01)

(52) U.S. Cl.
USPC ............... 502/60; 502/62; 502/64; 502/71; 502/77; 502/85

(58) Field of Classification Search
USPC .................. 502/60, 62, 85, 64, 71, 77
See application file for complete search history.

(56) References Cited

U.S. PATENT DOCUMENTS

| | | | |
|---|---|---|---|
| 3,442,795 A | 5/1969 | Kerr et al. | |
| 4,083,886 A | 4/1978 | Michalko | |
| 4,371,714 A | 2/1983 | Young | |
| 4,419,220 A | 12/1983 | LaPierre et al. | |
| 4,469,908 A | 9/1984 | Burress | |
| 4,891,458 A | 1/1990 | Innes et al. | |
| 4,954,243 A | 9/1990 | Kuehl et al. | |
| 5,019,543 A * | 5/1991 | Davis et al. | 502/64 |
| 5,118,897 A | 6/1992 | Khonsari et al. | |
| 5,196,574 A | 3/1993 | Kocal | |
| 5,200,168 A | 4/1993 | Apelian et al. | |
| 5,242,676 A | 9/1993 | Apelian et al. | |
| 5,284,989 A | 2/1994 | Apelian et al. | |
| 5,304,695 A | 4/1994 | Haag et al. | |
| 5,310,534 A | 5/1994 | Fajula et al. | |
| 5,321,194 A | 6/1994 | Apelian et al. | |
| 5,567,666 A * | 10/1996 | Beck et al. | 502/71 |
| 5,723,710 A | 3/1998 | Gajda et al. | |
| 5,874,647 A | 2/1999 | McGhee et al. | |
| 5,929,295 A | 7/1999 | Wu et al. | |
| 5,980,859 A * | 11/1999 | Gajda et al. | 423/713 |
| 6,025,293 A | 2/2000 | Wu et al. | |
| 6,315,964 B1 | 11/2001 | Knifton et al. | |
| 6,617,481 B1 | 9/2003 | Kulprathipanja et al. | |
| 6,620,402 B2 | 9/2003 | Jacobsen et al. | |
| 7,253,331 B2 | 8/2007 | Martens et al. | |
| 2002/0049359 A1* | 4/2002 | Timken et al. | 585/455 |

FOREIGN PATENT DOCUMENTS

| | | |
|---|---|---|
| EP | 0259526 | 3/1988 |
| WO | WO 93/00317 | 1/1993 |

OTHER PUBLICATIONS

International Preliminary Report on Patentability for PCT/US2009/059353 mailed Jul. 28, 2011.
Supplementary European Search Report for Application No. EP 09 83 8536 dated Dec. 12, 2011.

* cited by examiner

*Primary Examiner* — Elizabeth Wood
(74) *Attorney, Agent, or Firm* — Alix, Yale & Ristas, LLP

(57) ABSTRACT

A catalyst useful for the alkylation or transalkylation of aromatic compounds is disclosed. The catalyst is an acid-treated zeolitic catalyst produced by a process including contacting an acidic zeolitic catalyst comprising surface non-framework aluminum and framework aluminum with an organic dibasic acid at a catalyst to acid weight ratio in the range from about 2:1 to about 20:1 and at a temperature in the range from about 50° C. to about 100° C. to selectively remove at least a portion of the surface non-framework aluminum. The resulting catalyst may have a measured first-order rate constant, $k_{cum}$, for the alkylation of benzene with propylene to form cumene, of at least 2.0 cm$^3$/s g.

15 Claims, 1 Drawing Sheet

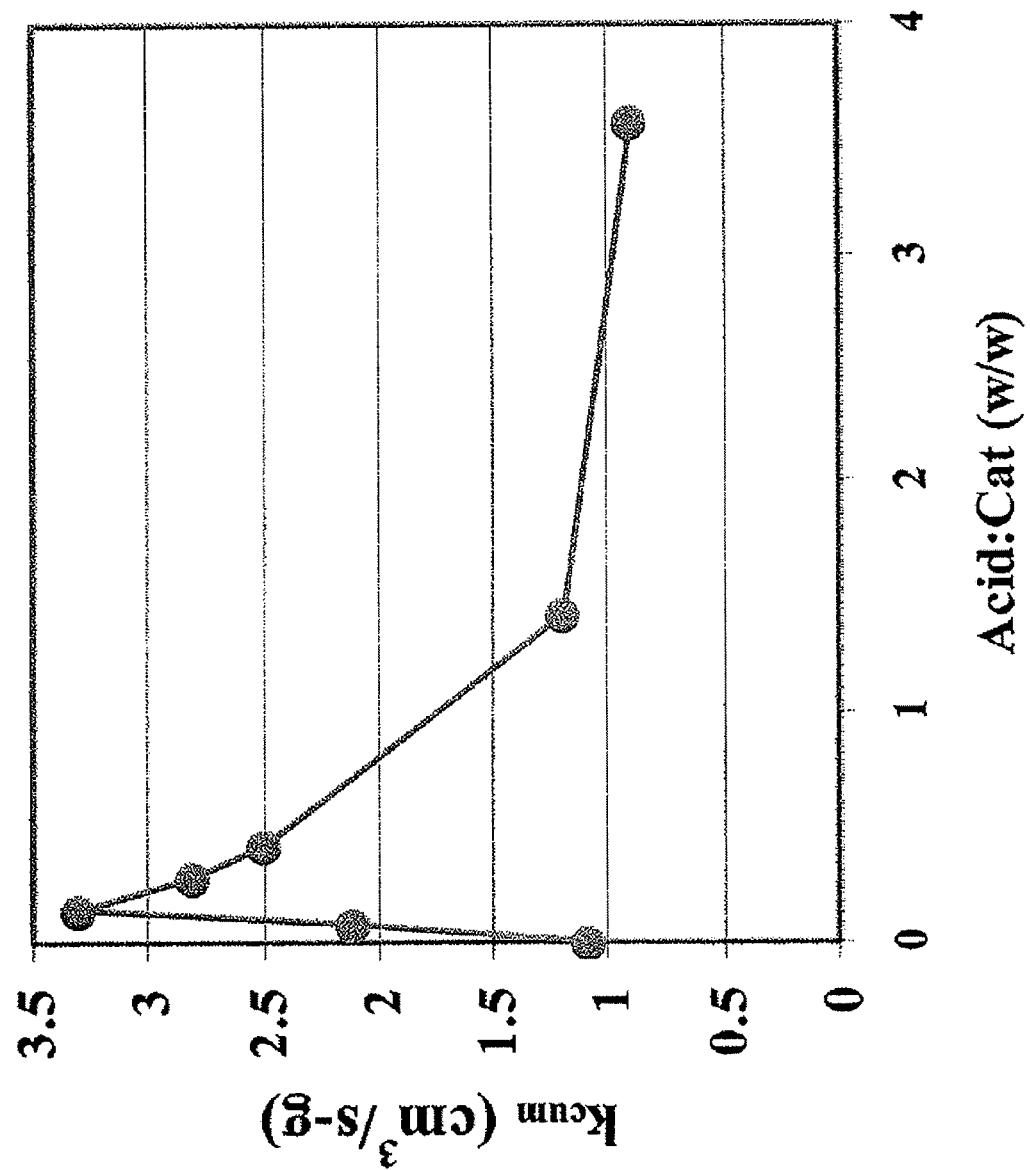

CATALYSTS USEFUL FOR THE ALKYLATION OF AROMATIC HYDROCARBONS

BACKGROUND OF DISCLOSURE

1. Field of the Disclosure

Embodiments disclosed herein relate generally to a process for the alkylation or transalkylation of aromatic compounds with olefins, alcohols and/or alkyl halides. In another aspect, embodiments disclosed herein relate to a process for the production of catalysts useful for the alkylation or transalkylation of aromatic compounds.

2. Background

Alkylation refers generally to a type of chemical reaction resulting in addition of an alkyl group to an organic compound. Olefins, such as ethylene, propylene, and butylenes, are well-known alkylating agents, frequently used in synthesis of alkylated derivatives. Alkylation of benzene is a commercially important process, used to increase the octane rating of fuel and to produce valuable chemical feedstocks. For example, alkylation of benzene with ethylene may be used to produce ethylbenzene, which may be subsequently converted to styrene. Similarly, alkylation of benzene with propylene may be used to produce cumene, which may be subsequently converted to phenol and acetone.

A typical benzene alkylation reaction is shown below:

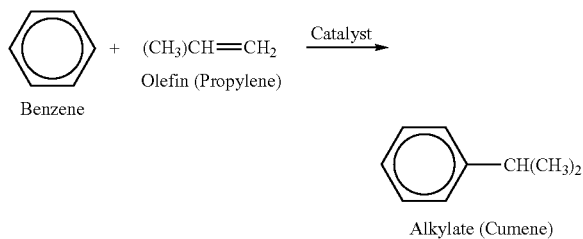

Alkylation technology, still widely employed in the petrochemical industry, involves the use of a catalyst based on phosphoric acid. Newer technology utilizes non-polluting, non-corrosive, regenerable materials, such as zeolitic molecular sieve catalysts. U.S. Pat. Nos. 4,371,714 and 4,469,908 disclose straight pass alkylation of aromatic compounds using molecular sieve catalysts in fixed beds. However, there are two main problems arising from the use of zeolitic catalysts in alkylation reactions, namely a rapid deactivation of the zeolitic catalyst due to coking and poisoning and a higher yield of polyalkylated by-products. Other patents discussing use of zeolitic catalysts for alkylation and transalkylation may include U.S. Pat. Nos. 5,118,897, 4,083,886, and 4,891,458, among others.

Zeolitic materials, both natural and synthetic, have been demonstrated to have catalytic properties for various types of hydrocarbon conversion, including alkylation as mentioned above. It is often advantageous to dealuminate these materials in order to improve their process performance. Performance measures typically improved following dealumination include product selectivity, product quality and catalyst stability.

Conventional techniques for zeolite dealumination include hydrothermal treatment, mineral acid treatment with HCl, HNO$_3$, and H$_2$SO$_4$, and chemical treatment with SiCl$_4$ or ethylenediaminetetraacetic acid (EDTA). The treatments are limited, in many cases, in the extent of dealumination by the onset of crystal degradation and loss of sorption capacity.

U.S. Pat. No. 4,419,220 discloses that dealumination of zeolite Beta via treatment with HCl solutions is limited to SiO$_2$/Al$_2$O$_3$ ratios of about 200 to 300 beyond which significant losses to zeolite crystallinity are observed.

U.S. Pat. No. 3,442,795 describes a process for preparing highly siliceous zeolite-type materials from crystalline aluminosilicates by means of a solvolysis, e.g. hydrolysis, followed by a chelation. In this process, the acid form of a zeolite is subjected to hydrolysis, to remove aluminum from the aluminosilicate. The aluminum can then be physically separated from the aluminosilicate by the use of complexing or chelating agents such as ethylenediaminetetraacetic acid or carboxylic acid, to form aluminum complexes that are readily removable from the aluminosilicate. The examples are directed to the use of EDTA to remove alumina.

EP 0 259 526 B1 discloses the use of dealumination in producing ECR-17. The preferred dealumination method involves a combination of steam treatment and acid leaching, or chemical treatments with silicon halides. The acid used is preferably a mineral acid, such as HCl, HNO$_3$ or H$_2$SO$_4$, but may also be weaker acids such as formic, acetic, citric, oxalic, tartaric acids and the like.

U.S. Pat. No. 5,310,534 discloses the dealumination of zeolites using strong inorganic and organic acids, such as formic acid, trichloroacetic acid, trifluoracetic acid, hydrochloric acid, sulfuric acid, and nitric acid.

U.S. Pat. No. 5,874,647 discloses a process for preparing a zeolite catalyst including hydrothermally treating a catalyst with a gas including water and inert components at an elevated temperature followed by treating of the catalyst with an acid, such as nitric, oxalic, hydrochloric, methanesulfonic, fluorosulfonic, and hydrofluoric acid.

U.S. Pat. No. 6,620,402 discloses a process including the dealumination of zeolites by removal of the zeolite framework or crystal structure, such as obtained by removal of the Al$^{+3}$ ions. Dealuminizing agents include mineral acids, polyvalent acids, and chelating agents, such as an ammonium-containing agent.

Other various patents describing aluminum extraction from a zeolite may include U.S. Pat. Nos. 4,954,243, 5,242,676, 5,200,168, 5,304,695, 5,567,666, 5,929,295, 6,025,293, 5,723,710, and 5,321,194.

Conditions used in many prior art dealumination processes may result in loss of high acidity framework aluminum sites within the catalyst, which additionally results in a loss of catalyst activity. Accordingly, there exists a need for dealumination processes that may selectively remove only a portion of the alumina, non-framework aluminum, enhancing the accessibility to the strong acidic sites contained in the zeolitic structure.

SUMMARY OF THE DISCLOSURE

In one aspect, embodiments disclosed herein relate to a method for improving the activity of acidic zeolitic catalysts, the method including: contacting an acidic zeolitic catalyst comprising surface non-framework aluminum and framework aluminum with an organic dibasic acid at a catalyst to acid weight ratio in the range from about 2:1 to about 20:1 and at a temperature in the range from about 50° C. to about 100° C. for a duration of up to about 2 hours to selectively remove at least a portion of the surface non-framework aluminum, thereby forming a selectively dealuminated zeolitic catalyst.

The selectively dealuminated zeolitic catalyst may have a measured first-order rate constant, $k_{cum}$, for the alkylation of benzene with propylene to form cumene, of at least 2.0 cm$^3$/s g.

In another aspect, embodiments disclosed herein relate to a process for the alkylation or transalkylation of aromatic hydrocarbons, including: contacting a) at least one $C_{6+}$ aromatic hydrocarbon and b) at least one of an olefin, an alcohol, and an alkyl halide with c) an acid-treated zeolitic catalyst under conditions of temperature and pressure to produce at least one of an alkylate product and a transalkylate product; wherein the acid-treated zeolitic catalyst is produced by a process including contacting an acidic zeolitic catalyst comprising surface non-framework aluminum and framework aluminum with an organic dibasic acid at a catalyst to acid weight ratio in the range from about 2:1 to about 20:1 and at a temperature in the range from about 50° C. to about 100° C. to selectively remove at least a portion of the surface non-framework aluminum.

In another aspect, embodiments disclosed herein relate to a catalyst useful for the alkylation or transalkylation of aromatic compounds, the catalyst comprising an acid-treated zeolitic catalyst produced by a process including: contacting an acidic zeolitic catalyst comprising surface non-framework aluminum and framework aluminum with an organic dibasic acid at a catalyst to acid weight ratio in the range from about 2:1 to about 20:1 and at a temperature in the range from about 50° C. to about 100° C. to selectively remove at least a portion of the surface non-framework aluminum.

Other aspects and advantages will be apparent from the following description and the appended claims.

BRIEF DESCRIPTION OF DRAWINGS

FIG. 1 presents test results comparing activity of selectively dealuminated zeolitic catalysts according to embodiments disclosed herein with untreated zeolitic catalysts.

DETAILED DESCRIPTION

In one aspect, embodiments herein relate to a process for the alkylation or transalkylation of aromatic compounds with olefins, alcohols and/or alkyl halides. In another aspect, embodiments disclosed herein relate to a process for the production of catalysts useful for the alkylation or transalkylation of aromatic compounds.

Catalysts useful in embodiments disclosed herein include acidic zeolitic catalysts, such as silica-aluminas and aluminosilicates, that have been treated with an organic dibasic acid to selectively remove a portion of the aluminum from the catalyst. Aluminum-containing catalysts useful herein may be characterized as having a crystalline framework structure composed of an assembly of silicon and aluminum atoms, each surrounded by a tetrahedron of shared oxygen atoms, and a precisely defined pore structure. Exchangeable cations may be present in the pores. In addition to the framework aluminum, aluminum containing catalysts useful in embodiments disclosed herein may have non-framework or extra-framework aluminum that is not integral with the crystalline framework structure. Treatment of acidic zeolitic catalysts with organic dibasic acids according to methods described herein may selectively remove the non-framework aluminum, thus increasing the overall acidity of the catalyst. In some embodiments, the acid treatment may be performed under conditions such that only non-framework aluminum is removed from the catalyst, extracting essentially no aluminum from the framework of the catalyst.

The catalysts may also contain one or more optional elements, including titanium, zirconium, hafnium, tantalum, and niobium, in an amount from about 0 weight percent up to about 10 weight percent; from about 0.01 weight percent to about 3 weight percent in other embodiments. These optional elements may be incorporated into the catalyst material prior to selective dealumination or introduced to the material after selective dealumination.

The selectively dealuminated catalysts according to embodiments disclosed herein may be prepared by contacting an acidic zeolitic catalyst comprising surface non-framework aluminum and framework aluminum with an organic dibasic acid to selectively remove at least a portion of the surface non-framework aluminum. The amount of organic dibasic acid required for the selective dealumination may depend on the detailed composition of a given acidic zeolitic catalyst and it physical properties. In general, the amount of organic dibasic acid used during the treating step may be at a catalyst to acid weight ratio in the range from about 1.5:1 to about 20:1 in some embodiments. In other embodiments, the catalyst to acid ratio may be in the range from about 2:1 to about 20:1; from about 2:1 to about 15:1 in other embodiments; from about 2.5:1 to about 12:1 in other embodiments; from about 3.5:1 to about 10:1 in other embodiments; and from about 6:1 to about 8:1 in yet other embodiments.

The acidic zeolitic catalyst may be contacted with the organic dibasic acid solution for a time ranging from 5 minute to 2 hours in some embodiments; from 30 minutes to 90 minutes in other embodiments. The selective dealumination of acidic zeolitic catalysts may be performed in a single step or multiple steps. The selective dealumination may be performed at relatively mild conditions, such as at a temperature in the range from about 50° C. to about 100° C. in some embodiments; at a temperature in the range from about 65° C. to about 90° C. in other embodiments. During contact with the organic dibasic acid, the slurry may be stirred continuously or intermittently.

Following contact with the organic dibasic acid for the selective dealumination, the excess solution in the treatment vessel should be drained, and the selectively dealuminated catalyst may be washed with sufficient amounts of clean, deionized water. The catalyst may then be dried, such as at a temperature in the range from about 80° C. to about 150° C.

Acidic zeolitic catalysts that may be selectively dealuminated according to embodiments disclosed herein may include natural and synthetic zeolites. Acidic crystalline zeolitic structures useful in embodiments disclosed herein may be obtained by the building of a three dimensional network of $AlO_4$ and $SiO_4$ tetrahedra linked by the sharing of oxygen atoms. The framework thus obtained contains pores, channels and cages or interconnected voids. As trivalent aluminum ions replace tetravalent silicon ions at lattice positions, the network bears a net negative charge, which must be compensated for by counterions (cations). These cations are mobile and may occupy various exchange sites depending on their radius, charge or degree of hydration, for example. They can also be replaced, to various degrees, by exchange with other cations. Because of the need to maintain electrical neutrality, there is a direct 1:1 relationship between the aluminum content of the framework and the number of positive charges provided by the exchange cations. When the exchange cations are protons, the zeolite is acidic. The acidity of the zeolite is therefore determined by the amount of proton exchanged for other cations with respect to the amount of aluminum.

Zeolitic catalysts that may be used in some embodiments disclosed herein may include large pore size zeolites, intermediate pore size zeolites, and small pore size zeolites. These zeolites are described in "Atlas of Zeolite Structure Types," eds. W. H. Meier and D. H. Olson, Butterworth-Heineman, Third Edition, 1992, which is hereby incorporated by reference. A large pore zeolite generally has a pore size greater than about 7 Å and includes for example LTL, VFI, MAZ, MEI, FAU, EMT, OFF, BEA, and MOR structure type zeolites (IUPAC Commission of Zeolite Nomenclature). Examples of large pore zeolites, include, for example, mazzite, mordenite, offretite, zeolite L, VPI-5, zeolite Y, zeolite X, omega, Beta, ZSM-3, ZSM-4, ZSM-18, and ZSM-20. An intermediate pore size zeolite generally has a pore size from about 5 Å, to about 7 Å and includes for example, MFI, MFS, MEL, MTW, EUO, MTT, HEU, FER, and TON structure type zeolites (IUPAC Commission of Zeolite Nomenclature). Examples of intermediate pore size zeolites, include ZSM-5, ZSM-12, ZSM-22, ZSM-23, ZSM-34, ZSM-35, ZSM-38, ZSM-48, ZSM-50, silicalite, and silicalite 2. A small pore size zeolite generally has a pore size from about 3 Å to about 5.0 Å and includes for example, CHA, ERI, KFI, LEV, and LTA structure type zeolites (IUPAC Commission of Zeolite Nomenclature). Examples of small pore zeolites include ZK-4, ZK-14, ZK-21, ZK-22, ZK-5, ZK-20, zeolite A, erionite, chabazite, zeolite T, gemlinite, and clinoptilolite.

Clay or amorphous catalysts including silica-alumina and fluorided silica-alumina may also be used. Further discussion of alkylation catalysts may be found in U.S. Pat. Nos. 5,196,574; 6,315,964 and 6,617,481. Various types of zeolitic catalysts may be used for alkylation as well as other types of catalytic refinery processes. FCC processes may utilize at least one of a type Y, Beta, and ZSM-5, for example. The FCC zeolitic catalyst typically contains three parts: the zeolite, typically about 30 to 50 wt. % of the catalyst particle, an active matrix, and a binder. In one embodiment, the particle size of the FCC catalyst may be between 50 and 60 microns. In another embodiment, the zeolitic catalyst may initially come in ammonium form, which may be converted to the $H^+$ form by heating at over 300° C. before being used as an alkylation catalyst. One must take care not to overheat the catalyst prior to alkylation, because excessive temperature may dealuminate the zeolite and shrink the ring structures, which may reduce the activity for alkylation. In addition to zeolitic catalyst, inorganic catalyst, such as sulfated zirconia or tungstated zirconia, may be used for alkylation as well. Other useful zeolitic catalysts may include ZSM-22, ZSM-23, MCM-22, and MCM-49.

In some embodiments, suitable catalysts for alkylation and transalkylation may include metal stabilized catalysts. For example, such catalysts may include a zeolite component, a metal component, and an inorganic oxide component. The zeolite may be a pentasil zeolite, which include the structures of MFI, MEL, MTW, MTT and FER (IUPAC Commission on Zeolite Nomenclature), MWW, a beta zeolite, or a mordenite. The metal component typically is a noble metal or base metal, and the balance of the catalyst may be composed of an inorganic oxide binder, such as alumina. Other catalysts having a zeolitic structure that may be used in embodiments disclosed herein are described in, for example, U.S. Pat. No. 7,253,331, which is hereby incorporated by reference.

Prior to or following selective dealumination, the acidic zeolitic catalyst may be composited with a porous matrix material, such as alumina, silica, titania, zirconia, silica-alumina, silica-magnesia, silica-zirconia, silica-thoria, silica-beryllia, silica-titania as well as ternary compositions, such as silica-alumina-thoria, silica-alumina-zirconia, silica-alumina-magnesia, and silica-magnesia-zirconia. The matrix may be in the form of a cogel. The relative proportions of zeolite component and inorganic oxide gel matrix may vary widely with the zeolite content ranging from between 1 to 99, more usually 5 to 80, percent by weight of the composite.

Organic dibasic acids useful for selective dealumination processes according to embodiments disclosed herein may include various dicarboxylic acids. Suitable acids may include oxalic, malonic, succinic, glutaric, adipic, tartaric, maleic, phthalic, or mixtures thereof. Other useful carboxylic acids may include 1,2-cyclopentane dicarboxylic acid, fumaric acid, itaconic acid, phthalic acid, terephthalic acid, phenylmalonic acid, hydroxyphtalic acid, dihydroxyfumaric acid, tricarballylic acid, and benzene-1,3,5-tricarboxylic acid. The dicarboxylic acid may be used in solution, such as an aqueous dicarboxylic acid solution. Tricarboxylic acids such as citric acid and higher polycarboxylic acids can also be used. More than one acid treatment step may be used to attain the desired selective dealumination in the processes disclosed herein.

As a result of dealumination at conditions suitable to selectively dealuminate only non-framework aluminum, catalysts according to embodiments disclosed herein may exhibit exceptionally high activity for alkylation and transalkylation reactions, such as the alkylation of benzene with propylene to form cumene. For example, selectively dealuminated catalysts according to embodiments disclosed herein may have an activity, as measured under controlled test conditions as described in the test procedures below (Examples), where the first-order rate constant $k_{cum}$, is at least 2 cm$^3$/s g. In other embodiments, the first-order rate constant $k_{cum}$, may be at least 2.25 cm$^3$/s g; at least 2.5 cm$^3$/s g in other embodiments; at least 3 cm$^3$/s g in other embodiments; at least 3.25 cm$^3$/s g in other embodiments; at least 3.5 cm$^3$/s g in other embodiments; and at least 4 cm$^3$/s g in other embodiments.

For example, in some embodiments, a beta zeolite may be selectively dealuminated according to embodiments disclosed herein, resulting in a selectively dealuminated catalyst having a first-order rate constant $k_{cum}$, of at least 2 cm$^3$/s g; at least 2.1 cm$^3$/s g in other embodiments; at least 2.2 cm$^3$/s g in other embodiments; at least 2.5 cm$^3$/s g in other embodiments; and at least 3 cm$^3$/s g in other embodiments.

As another example, in some embodiments, a high performance beta zeolite may be selectively dealuminated according to embodiments disclosed herein, resulting in a selectively dealuminated catalyst having a first-order rate constant $k_{cum}$, of at least 2.5 cm$^3$/s g; at least 3 cm$^3$/s g in other embodiments; at least 3.5 cm$^3$/s g in other embodiments; at least 3.75 cm$^3$/s g in other embodiments; and at least 4 cm$^3$/s g in other embodiments.

Selective dealumination of catalysts according to embodiments disclosed herein, may thus be produced by a process including: forming an aqueous solution of the organic dibasic acid; admixing the acidic zeolitic catalyst with the aqueous solution for the contacting; separating the acid-contacted zeolitic catalyst from the aqueous solution; washing the acid-contacted catalyst to remove any excess organic dibasic acid; and drying the washed catalyst at a temperature in the range from about 80° C. to about 150° C.

Further, due to the treatment conditions and acid:catalyst dosages used herein, additional processing steps commonly used to dealuminate zeolite catalysts may be eliminated. For example, many prior art dealumination processes include hydrothermal treatment of the zeolite, or other pre-treatment steps, prior to acid treatment. Selective dealumination according to embodiments disclosed herein may be performed without such pre-treatment steps while resulting in a catalyst having an exceptionally high activity. Thus, processes to manufacture catalysts according to embodiments disclosed herein may be performed absent a hydrothermal treatment step or other common pre-treatment steps used for the dealumination of a zeolite.

The above-described selectively dealuminated catalysts may be used for the alkylation or transalkylation of aromatic compounds with various alkylation agents, including olefins, alcohols, and alkyl halides. Such catalysts may additionally find use in processes for the alkylation of isoparaffins with olefins and/or alcohols, as well as in fluid catalytic cracking (FCC) processes or hydrocracking processes.

In some embodiments of the alkylation and transalkylation processes described herein, olefins are reacted with aromatic hydrocarbons, such as benzene, to form an alkylate or transalkylate product. In some embodiments, olefins for the alkylation or transalkylation of aromatic hydrocarbon are those containing 2 to 6 carbon atoms. In other embodiments, olefins for the alkylation or transalkylation of aromatic hydrocarbon are those containing 2 to 4 carbon atoms, such as ethylene, propylene, butene-1, trans-butene-2 and cis-butene-2, or mixtures thereof.

The olefin feed streams used in various embodiments disclosed herein may also contain certain impurities, such as the corresponding $C_2$ to $C_4$ paraffins. Typically, the impurities, including dienes, acetylenes, water, sulfur compounds or nitrogen compounds which may be present in the olefin feedstock stream, are removed prior to the alkylation and transalkylation reaction to prevent rapid catalyst deactivation. In some cases, however, it may be desirable to add, in a controlled fashion, small amounts of water or nitrogen compounds to optimize catalytic properties.

In other embodiments, olefins useful in embodiments disclosed herein may include up to 20 carbon atoms. For example, olefins having greater than 6 carbon atoms may be used.

Alcohols useful in embodiments disclosed herein may include $C_1$ to $C_6$ primary and secondary alcohols. The term "alcohol" includes lower alkyl alcohols capable of forming azeotropes with the saturated and unsaturated hydrocarbons, in particular the $C_3$ to $C_7$ hydrocarbons, of the hydrocarbon feedstock. Examples of alcohols useful in embodiments disclosed herein include methanol, ethanol, n-propanol, i-propanol, n-butanol, i-butanol and t-butanol. In some embodiments, methanol may be used in combination with one or more of the $C_{2+}$ alcohols.

Alkyl halides useful in embodiments disclosed herein may include mono- or poly-halogenated $C_2$ to $C_6$ hydrocarbons, such as alkyl chlorides and alkyl bromides. For example, alkyl halides useful in embodiments disclosed herein may include methyl, ethyl, propyl, and butyl halides, their higher homologs, and their isomers.

In embodiments of the alkylation processes disclosed herein, a hydrocarbon feedstock containing aromatics, such as benzene, is reacted with olefins in the presence of an alkylation catalyst to form alkyl benzenes, which may be useful as specialty chemical feedstocks or as a high-octane gasoline component. In particular, one embodiment described herein involves reaction of benzene with a $C_2$ to $C_4$ olefin to form monoalkylate product in the presence of an alkylation catalyst. The precise process steps and process conditions may vary depending upon the catalyst system used. In another embodiment, a heterogeneous slurry catalyst is used to facilitate the alkylation reaction. For the purpose of illustration and not a limitation of the process, several representative alkylation reactions of olefins with benzene are provided as follows:

1) ethylene+benzene→ethylbenzene
2) propylene+benzene→isopropylbenzene (cumene)
3) n-butylene+benzene→butylbenzene
4) isobutylene+benzene→isobutylbenzene In addition to the monoalkylate product, alkylation reactions typically yield other undesirable byproducts in the form of heavy hydrocarbons, including but not limited to, polyalkylate, heavy flux oil (including components that will not transalkylate), and polymerized feed olefins.

Transalkylation reactions may be used to produce monoalkylate product by reacting benzene with polyalkylate. When transalkylation is desired, the transalkylating agent is a polyalkylate aromatic hydrocarbon containing two or more alkyl groups that each may have from 2 to about 4 carbon atoms. For example, suitable polyalkylate aromatic hydrocarbons include di-, tri- and tetra-alkyl aromatic hydrocarbons, such as diethylbenzene, triethylbenzene, diethylmethylbenzene (diethyltoluene), diisopropylbenzene, triisopropylbenzene, diisopropyltoluene, dibutylbenzene, and the like. In one particular embodiment, the polyalkylate aromatic hydrocarbon is diisopropylbenzene, which reacts with benzene to form cumene (isopropylbenzene).

Reaction products that may be obtained from the transalkylation process of benzene include, but are not limited to, ethylbenzene from the reaction of benzene with either ethylene or polyethylbenzenes; cumene from the reaction of benzene with propylene or polyisopropylbenzenes; ethyltoluene from the reaction of toluene with ethylene or polyethyltoluenes; cymenes from the reaction of toluene with propylene or polyisopropyltoluenes; and sec-butylbenzene from the reaction of benzene and n-butylene or polybutylbenzenes. For the purpose of illustration and not a limitation of the process, several representative transalkylation reactions of polyalkylate with benzene are provided as follows:

1) diethylbenzene+benzene→2 ethylbenzene
2) di-isopropylbenzene+benzene→2 isopropylbenzene (cumene)
3) dibutylbenzene+benzene→2 butylbenzene Various types of reactors can be used in the process of alkylation as well as transalkylation. Selection of the type of reactor for use in alkylation or transalkylation reaction may depend on a number of factors, including the desired mode of operation, throughput volume, and reaction control parameters, such as residence time and product yield.

Large scale industrial processes typically use continuous flow reactors, either as fixed bed or as moving bed reactors. Moving bed reactors typically operate either with concurrent or countercurrent catalyst, olefin, and hydrocarbon flows. These reactors may contain a single catalyst bed or multiple beds and may be equipped for the interstage addition of olefins and interstage cooling. Interstage olefin addition and more nearly isothermal operation enhance product quality and catalyst life. A moving bed reactor makes possible the continuous removal of spent catalyst for regeneration and replacement by fresh or regenerated catalysts.

In a moving bed reactor, alkylation is completed in a relatively short reaction zone following the introduction of olefin. Ten to thirty percent of the reacting aromatic molecules may be alkylated more than once. Transalkylation is a slower reaction which occurs both in the transalkylation and the alkylation reaction zones. If transalkylation proceeds to equilibrium, better than 90 wt % selectivity to monoalkylated product is generally achieved. Thus, transalkylation increases the yield of monoalkylated product by reacting the polyalkylated products with benzene.

In the selective monoalkylation of aromatics by olefins as catalyzed by the selectively dealuminated catalysts according to embodiments disclosed herein, the olefins, alcohols, and alkyl halides may contain from 2 up to at least 20 carbon atoms, and may be branched or linear, either terminal or internal. Thus, the specific nature of the alkylating agent is not particularly important.

Benzene is by far the most important representative of the alkylatable aromatic compounds which may be used in embodiments disclosed herein. More generally the aromatic compounds may be selected from the group consisting of benzene, naphthalene, anthracene, phenanthrene, and substituted derivatives thereof. The most important class of substituents found on the aromatic nucleus of alkylatable aromatic compounds are alkyl moieties containing from 1 up to about 20 carbon atoms. Another important substituent is the hydroxyl moiety as well as the alkoxy moiety whose alkyl group also contains from 1 up to 20 carbon atoms. Where the substituent is an alkyl or alkoxy group, a phenyl moiety also can be substituted on the paraffinic chain. Although unsubstituted and monosubstituted benzenes, naphthalenes, anthracenes, and phenanthrenes are most often used in the practice of this invention, polysubstituted aromatics also may be employed. Examples of suitable alkylatable aromatic compounds in addition to those cited above include biphenyl, toluene, xylene, ethylbenzene, propylbenzene, butylbenzene, pentylbenzene, hexylbenzene, heptylbenzene, octylbenzene, and so forth; phenol, cresol, anisole, ethoxy-, propoxy-, butoxy-, pentoxy-, hexoxybenzene, and so forth.

Alkylation conditions may include pressures in the range between about 200 and about 1,000 psig (1379-6985 kPa) but usually is in a range between about 300-600 psig (2069-4137 kPa). Representative alkylation temperatures include a range of between 200-250° C. for alkylation of benzene with ethylene and temperatures of 90-200° C. for the alkylation of benzene by propylene. The temperature range appropriate for alkylation of the alkylatable aromatic compounds of our invention with the olefins in the C2-C20 range is between about 60 and about 400° C., with the most usual temperature range being between about 90 and 250° C.

The ratio of alkylatable aromatic compound to alkylating agent used in the process may depend upon the degree of selective monoalkylation desired as well as the relative costs of the aromatic and olefinic components of the reaction mixture. For alkylation of benzene by propylene, benzene-to-olefin ratios may be as low as about 1 and as high as about 10, with a ratio of 2.5-8 being preferred. Where benzene is alkylated with ethylene a benzene-to-olefin ratio between about 1:1 and 8:1 is preferred. For detergent range olefins of C6-C20, a benzene-to-olefin ratio of between 5:1 up to as high as 30:1 is generally sufficient to ensure the desired monoalkylation selectivity, with a range between about 8:1 and about 20:1 even more highly desired.

As previously mentioned, catalysts according to embodiments disclosed herein may also be used to catalyze transalkylation as well as alkylation. By "transalkylation" is meant that process where an alkyl group on one aromatic nucleus is intermolecularly transferred to a second aromatic nucleus. The transalkylation of particular interest here is one where one or more alkyl groups of a polyalkylated aromatic compound is transferred to a nonalkylated aromatic compound, and is exemplified by reaction of diisopropylbenzene with benzene to afford two molecules of cumene. Thus, transalkylation often is utilized to add to the selectivity of a desired selective monoalkylation by reacting the polyalkylates invariably formed during alkylation with nonalkylated aromatic to form additional monoalkylated products. For the purposes of this section the polyalkylated aromatic compounds are those formed in the alkylation of alkylatable aromatic compounds with olefins as described above, and the nonalkylated aromatic compounds are benzene, naphthalene, anthracene, and phenanathrene. The reaction conditions for transalkylation are similar to those for alkylation, with temperatures being in the range of 100 to about 250° C., pressures in the range of 100 to about 750 psig, and the molar ratio of unalkylated aromatic to polyalkylated aromatic being in the range from about 1 to about 10. Examples of polyalkylated aromatics which may be reacted with, e.g., benzene as the nonalkylated aromatic include diethylbenzene, diisopropylbenzene, dibutylbenzene, triethylbenzene, triisopropylbenzene, and so forth.

EXAMPLES

Testing Procedures for Cumene Application

The catalytic activity of the zeolite beta catalysts was evaluated in the reaction of benzene alkylation with propylene to form cumene. The test reactor was a recirculating differential fixed bed reactor (⅞ inch ID SS tube) and the test conditions were a pressure of 350 psig, a temperature of 170° C., and a recirculation rate of 200 grams/min. The test feed contained 0.35-0.45 wt. % propylene dissolved in benzene with a feed rate of 6.0 grams/min. The catalyst charge was 0.7 gram with a particle size of 12-20 mesh derived from 1.6 mm extrudates containing 80 wt % zeolite and 20 wt % binders. The catalyst was dried two hours at 350° C. before loading the reactor. The test was carried out for 7 to 8 hours with samples taken every 30 minutes for analysis by gas chromatography (GC). The first-order reaction rate constant k, was calculated to represent catalyst activity for the alkylation of benzene with propylene to form cumene.

Catalyst Preparation

Comparative Example 1

Commercial Beta

The Zeolite beta catalyst used in this example and Examples 1-7 was obtained from Zeolyst International Co. of Valley Forge, Pa. The catalyst as received was 1.6 mm extrudates containing 80 wt % zeolite and was resized to 12-20 mesh particles. A portion of the catalyst particles was tested for catalytic activity for alkylation of benzene with propylene to cumene using the procedure described above and the other portion of the catalyst particles was first subjected to the acid treatment as described in Example 1-7 and then evaluated, the results of which are listed in Table 1 and illustrated in FIG. 1.

Example 1

An aqueous solution formed by dissolving 0.50 gram of oxalic acid dihydrate in 200 mL of deionized (DI) water was heated to 70° C. Then 5.0 grams of catalyst particles from Comparative Example 1 were added to the solution and the resulting mixture was held at 70° C. for one hour with stirring. After cooling this mixture to 25° C., the solid materials were collected by vacuum filtration. The solids thus obtained were added to 500 mL of DI water and the resulting mixture was heated to 70° C. and held at this temperature for one hour with stirring. Finally, the solids were collected by vacuum filtration and oven dried overnight at 120° C.

Example 2

An aqueous solution formed by dissolving 1.0 gram of oxalic acid dihydrate in 200 mL of DI water was heated to 70°

C. Then 5.0 grams of catalyst particles from Comparative Example 1 were added to the solution and the resulting mixture was held at 70° C. for one hour with stirring. After cooling this mixture to 25° C., the solid materials were collected by vacuum filtration. The solids thus obtained were added to 500 mL of DI water and the resulting mixture was heated to 70° C. and held at this temperature for one hour with stirring. Finally, the solids were collected by vacuum filtration and oven dried overnight at 120° C.

Example 3

An aqueous solution formed by dissolving 2.0 gram of oxalic acid dihydrate in 200 mL of DI water was heated to 70% Then 5.0 grams of catalyst particles from Comparative Example 1 were added to the solution and the resulting mixture was held at 70° C. for one hour with stirring. After cooling this mixture to 25° C., the solid materials were collected by vacuum filtration. The solids thus obtained were added to 500 mL of DI water and the resulting mixture was heated to 70° C. and held at this temperature for one hour with stirring. Finally, the solids were collected by vacuum filtration and oven dried overnight at 120° C.

Example 4

An aqueous solution formed by dissolving 3.0 gram of oxalic acid dihydrate in 200 mL of DI water was heated to 70° C. Then 5.0 grams of catalyst particles from Comparative Example 1 were added to the solution and the resulting mixture was held at 70° C. for one hour with stirring. After cooling this mixture to 25° C., the solid materials were collected by vacuum filtration. The solids thus obtained were added to 500 mL of DI water and the resulting mixture was heated to 70° C. and held at this temperature for one hour with stirring. Finally, the solids were collected by vacuum filtration and oven dried overnight at 120° C.

Example 5

An aqueous solution formed by dissolving 10.0 gram of oxalic acid dihydrate in 200 mL of DI water was heated to 70° C. Then 5.0 grams of catalyst particles from Comparative Example 1 were added to the solution and the resulting mixture was held at 70° C. for one hour with stirring. After cooling this mixture to 25° C., the solid materials were collected by vacuum filtration. The solids thus obtained were added to 500 mL of DI water and the resulting mixture was heated to 70° C. and held at this temperature for one hour with stirring. Finally, the solids were collected by vacuum filtration and oven dried overnight at 120° C.

Example 6

An aqueous solution formed by dissolving 25.0 gram of oxalic acid dihydrate in 200 mL of DI water was heated to 70° C. Then 5.0 grams of catalyst particles from Comparative Example 1 were added to the solution and the resulting mixture was held at 70° C. for one hour with stirring. After cooling this mixture to 25° C., the solid materials were collected by vacuum filtration. The solids thus obtained were added to 500 mL of DI water and the resulting mixture was heated to 70° C. and held at this temperature for one hour with stirring. Finally, the solids were collected by vacuum filtration and oven dried overnight at 120° C.

Example 7

An aqueous solution formed by dissolving 0.87 gram of malonic acid in 200 mL of DI water was heated to 70° C. Then 5.0 grams of catalyst particles from Comparative Example 1 were added to the solution and the resulting mixture was held at 70° C. for one hour with stirring. After cooling this mixture to 25° C., the solid materials were collected by vacuum filtration. The solids thus obtained were added to 500 mL of DI water and the resulting mixture was heated to 70° C. and held at this temperature for one hour with stirring. Finally, the solids were collected by vacuum filtration and oven dried overnight at 120° C.

TABLE 1

| Example | Acid Treatment | | $k_{cum}$ |
|---|---|---|---|
| | Acid | Catalyst:Acid (w/w) | ($cm^3 \, C_3^-$/s-g) |
| Comparative Example 1 | — | — | 1.1 |
| 1 | Oxalic Acid | 14.0 | 2.1 |
| 2 | Oxalic Acid | 7.0 | 3.3 |
| 3 | Oxalic Acid | 3.5 | 2.8 |
| 4 | Oxalic Acid | 2.3 | 2.5 |
| 5 | Oxalic Acid | 0.7 | 1.2 |
| 6 | Oxalic Acid | 0.3 | 0.9 |
| 7 | Malonic Acid | 5.7 | 2.0 |

Comparative Example 2

High Performance Beta

The high performance beta ("HP" Beta) used in this example and Examples 8-19 was prepared in accordance with the method set forth in U.S. Pat. No. 6,809,055 in a form of 1.6 mm extrudates with 80 wt % zeolite and 20 wt % binder. The extrudates were resized to 12-20 mesh for reactor evaluation and for the acid treatment described in Examples 8-19. The testing results of this sample along with the acid-treated samples are summarized in Table 2.

Example 8

An aqueous solution formed by dissolving 0.50 gram of oxalic acid dihydrate in 200 mL of DI water was heated to 70° C. Then 5.0 grams of catalyst particles from Comparative Example 2 were added to the solution and the resulting mixture was held at 70° C. for one hour with stirring. After cooling this mixture to 25° C., the solid materials were collected by vacuum filtration. The solids thus obtained were added to 500 mL of DI water and the resulting mixture was heated to 70° C. and held at this temperature for one hour with stirring. Finally, the solids were collected by vacuum filtration and oven dried overnight at 120° C.

Example 9

An aqueous solution formed by dissolving 1.0 gram of oxalic acid dihydrate in 200 mL of DI water was heated to 70° C. Then 5.0 grams of catalyst particles from Comparative Example 2 were added to the solution and the resulting mixture was held at 70° C. for one hour with stirring. After cooling this mixture to 25° C., the solid materials were collected by vacuum filtration. The solids thus obtained were added to 500 mL of DI water and the resulting mixture was heated to 70° C. and held at this temperature for one hour with stirring. Finally, the solids were collected by vacuum filtration and oven dried overnight at 120° C.

Example 10

An aqueous solution formed by dissolving 2.0 grams of oxalic acid dihydrate in 200 mL of DI water was heated to 70°

C. Then 5.0 grams of catalyst particles from Comparative Example 2 were added to the solution and the resulting mixture was held at 70° C. for one hour with stirring. After cooling this mixture to 25° C., the solid materials were collected by vacuum filtration. The solids thus obtained were added to 500 mL of DI water and the resulting mixture was heated to 70° C. and held at this temperature for one hour with stirring. Finally, the solids were collected by vacuum filtration and oven dried overnight at 120° C.

Example 11

An aqueous solution formed by dissolving 25.0 grams of oxalic acid dihydrate in 200 mL of DI water was heated to 70° C. Then 5.0 grams of catalyst particles from Comparative Example 2 were added to the solution and the resulting mixture was held at 70° C. for one hour with stirring. After cooling this mixture to 25° C., the solid materials were collected by vacuum filtration. The solids thus obtained were added to 500 mL of DI water and the resulting mixture was heated to 70° C. and held at this temperature for one hour with stirring. Finally, the solids were collected by vacuum filtration and oven dried overnight at 120° C.

Example 12

An aqueous solution formed by dissolving 2.0 grams of oxalic acid dihydrate in 200 mL of DI water was heated to 85° C. Then 5.0 grams of catalyst particles from Comparative Example 2 were added to the solution and the resulting mixture was held at 85° C. for one hour with stirring. After cooling this mixture to 25° C., the solid materials were collected by vacuum filtration. The solids thus obtained were added to 500 mL of DI water and the resulting mixture was heated to 85° C. and held at this temperature for one hour with stirring. Finally, the solids were collected by vacuum filtration and oven dried overnight at 120° C.

Example 13

An aqueous solution was formed by dissolving 2.0 grams of oxalic acid dihydrate in 200 mL of DI water. Then 5.0 grams of catalyst particles from Comparative Example 2 were added to the solution and the resulting mixture was stirred one hour at 22° C. The solid materials were collected by vacuum filtration, washed with 500 mL of DI water, and oven dried overnight at 120° C.

Example 14

An aqueous solution was formed by dissolving 2.0 grams of oxalic acid dihydrate in 200 mL of DI water. Then 5.0 grams of catalyst particles from Comparative Example 2 were added to the solution and the resulting mixture was stirred six hours at 22° C. The solid materials were collected by vacuum filtration, washed with 500 mL of DI water, and oven dried overnight at 120° C.

Example 15

An aqueous solution (200 mL) containing 3.5 wt % $HNO_3$ was heated to 70° C. Then 5.0 gram of catalyst particles from Comparative Example 2 were added to the solution and the resulting mixture was stirred at 70° C. for one hour. After cooling this mixture to 25° C., the solid materials were collected by vacuum filtration. The solids thus obtained were added to 500 mL of DI water and the resulting mixture was heated to 70° C. and held at this temperature for one hour with stirring. Finally, the solids were collected by vacuum filtration and oven dried overnight at 120° C.

Example 16

An aqueous solution (200 mL) containing 0.7 wt % $HNO_3$ was heated to 70° C. Then 5.0 gram of catalyst particles from Comparative Example 2 were added to the solution and the resulting mixture was stirred at 70° C. for one hour. After cooling this mixture to 25° C., the solid materials were collected by vacuum filtration. The solids thus obtained were added to 500 mL of DI water and the resulting mixture was heated to 70° C. and held at this temperature for one hour with stirring. Finally, the solids were collected by vacuum filtration and oven dried overnight at 120° C.

Example 17

Catalyst particles (5.0 g) from Comparative Example 2 were added to an aqueous solution (200 mL) containing 0.7 wt % $HNO_3$ and the mixture was stirred at 22° C. for one hour. Then the catalyst particles were collected by vacuum filtration, washed with 500 mL of DI water, and oven dried overnight at 120° C.

Example 18

An aqueous solution formed by dissolving 1.35 grams of acetic acid in 200 mL of DI water was heated to 70° C. Then 5.0 gram of catalyst particles from Comparative Example 2 were added to the solution and the resulting mixture was held at 70° C. for one hour with stirring. After cooling the mixture to 25° C., the solid materials were collected by vacuum filtration. The solids thus obtained were added to 500 mL of DI water and the resulting mixture was heated to 70° C. and held at this temperature for one hour with stirring. Finally, the solids were collected by vacuum filtration and oven dried overnight at 120° C.

Example 19

An aqueous solution formed by dissolving 0.87 gram of malonic acid in 200 mL of DI water was heated to 70° C. Then 5.0 gram of catalyst particles from Comparative Example 2 were added to the solution and the resulting mixture was held at 70° C. for one hour with stirring. After cooling the mixture to 25° C., the solid materials were collected by vacuum filtration. The solids thus obtained were added to 500 mL of DI water and the resulting mixture was heated to 70° C. and held at this temperature for one hour with stirring. Finally, the solids were collected by vacuum filtration and oven dried overnight at 120° C.

TABLE 2

| Example | Acid | Catalyst:Acid (w/w) | Temperature (° C.) | Time (hr) | $k_{cum}$ (cm$^3$ C$_3^=$/s-g) |
|---|---|---|---|---|---|
| Comp. Example 2 | — | — | — | — | 2.0 |
| 8 | Oxalic Acid | 14.0 | 70 | 1 | 5.2 |
| 9 | Oxalic Acid | 7.0 | 70 | 1 | 10 |
| 10 | Oxalic Acid | 3.5 | 70 | 1 | 7.1 |
| 11 | Oxalic Acid | 0.3 | 70 | 1 | 0.9 |
| 12 | Oxalic Acid | 3.5 | 85 | 1 | 3.8 |
| 13 | Oxalic Acid | 3.5 | 22 | 1 | 2.2 |
| 14 | Oxalic Acid | 3.5 | 22 | 6 | 2.6 |
| 15 | Nitric Acid | 0.7 | 70 | 1 | 2.6 |
| 16 | Nitric Acid | 3.6 | 70 | 1 | 3.1 |
| 17 | Nitric Acid | 3.6 | 22 | 1 | 2.2 |
| 18 | Acetic Acid | 3.7 | 70 | 1 | 2.2 |
| 19 | Malonic Acid | 5.7 | 70 | 1 | 4.3 |

The test procedure and results for alkylation of linear alkylalkylbenzenes are shown below: Catalytic activity of the commercial beta (same sample as used in Comparative Example 1) and acid treated beta (same sample as used in Example 2) was evaluated. All the runs were carried out with a 1-liter autoclave equipped with a stirrer. For the alkylation of benzene with 1-dodecene, the reaction was carried out at 140° C. with 1.25 g of catalyst, 112 g of benzene, and 12 g of 1-dodecene. For the alkylation of benzene with pacolate, the reaction was also carried out at 140° C., but with 0.625 g catalyst, 60 g of benzene, and 60 g of pacolate which contains 50 g of paraffins (C10-C14) and 6 g of olefins (C10-C14). The reaction mixtures were analyzed at 2.5, 4.0, and 6.0 hr reaction time by GC and the conversions are summarized in Table 3.

TABLE 3

| Reaction | Reaction Time (hr) | Commercial Beta % Olefin Conversion | Acid-Treated Beta % Olefin Conversion |
|---|---|---|---|
| Alkylation of benzene with 1-dodecene | 2.5 | 63.8 | 77.0 |
| | 4.0 | 74.6 | 94.0 |
| | 6.0 | 82.6 | 95.3 |
| Alkylation of benzene with pacolate | 2.5 | 54.0 | 69.4 |
| | 4.0 | 67.9 | 86.6 |
| | 6.0 | 73.5 | 91.4 |

As described above, embodiments disclosed herein provide for zeolitic catalysts suitable for use in alkylation and transalkylation processes. The zeolitic catalysts are dealuminated at specified acid to catalyst ratios and reaction conditions to selectively remove at least a portion of the non-framework aluminum. In some embodiments, dealumination processes according to embodiments disclosed herein may advantageously remove essentially only surface non-framework aluminum while leaving the framework aluminum intact. Selective dealumination according to embodiments disclosed herein may enhance the strong acid sites contained in the catalyst. Thus, selectively dealuminated catalysts according to embodiments disclosed herein may have active acidic sites more readily accessible for the desired aromatic alkylation and transalkylation reactions.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed:

1. A method for improving the activity of acidic zeolitic catalysts, the method comprising:
    contacting an acidic zeolitic catalyst comprising at least one from the group consisting of zeolite Beta, ZSM-5, ZSM-22, ZSM-23, MCM-22, and MCM-49 having surface non-framework aluminum and framework aluminum with an organic dibasic acid at a catalyst to acid weight ratio in the range from about 2:1 to about 20:1 and at a temperature in the range from about 50° C. to about 100° C. for a duration of up to about 2 hours to selectively remove at least a portion of the surface non-framework aluminum, thereby forming a selectively dealuminated zeolitic catalyst;
    wherein the selectively dealuminated zeolitic catalyst has a measured first-order rate constant, $k_{cum}$, for the alkylation of benzene with propylene to form cumene, of at least 2.0 cm$^3$/s g.

2. The method of claim 1, further comprising:
    forming an aqueous solution of the organic dibasic acid;
    admixing the acidic zeolitic catalyst with the aqueous solution for the contacting;
    separating the acid-contacted zeolitic catalyst from the aqueous solution;
    washing the acid-contacted catalyst to remove any excess organic dibasic acid; and
    drying the washed catalyst at a temperature in the range from about 80° C. to about 150° C.

3. The method of claim 1, wherein the contacting a zeolitic catalyst with an organic dibasic acid removes essentially no surface framework aluminum.

4. The method of claim 1, wherein the catalyst to acid weight ratio is in the range from about 6:1 to about 8:1.

5. The method of claim 4, wherein the selectively dealuminated zeolitic catalyst has a measured first-order constant, $k_{cum}$, for the alkylation of benzene with propylene to form cumene, of at least 3 cm$^3$/s g.

6. The method of claim 1, wherein the organic dibasic acid comprises at least one of oxalic acid, malonic acid, glutaric acid, adipic acid, maleic acid, fumaric acid, tartaric acid, ethylene diamine tetra-acetic acid, and mixtures thereof.

7. The method of claim 1, wherein the zeolitic catalyst comprises at least one of a silica-alumina and an aluminosilicate.

8. The method of claim 1, wherein the contacting is at a temperature in the range from about 65° C. to about 90° C. and is performed for a duration of between 0.5 and 1.5 hours.

9. The method of claim 1, wherein the acidic zeolitic catalyst comprises high performance beta zeolite and wherein the selectively dealuminated zeolitic catalyst has a measured first-order rate constant, $k_{cum}$, for the alkylation of benzene with propylene to form cumene, of at least 4 cm$^3$/s g.

10. The method of claim 1, wherein the catalyst comprises zeolite Beta.

11. The method of claim 1, wherein the catalyst comprises ZSM-5.

12. The method of claim 1, wherein the catalyst comprises ZSM-22.

13. The method of claim 1, wherein the catalyst comprises ZSM-23.

14. The method of claim 1, wherein the catalyst comprises MCM-22.

15. The method of claim 1, wherein the catalyst comprises MCM-49.

\* \* \* \* \*